United States Patent

Curtis et al.

[11] 3,971,335
[45] July 27, 1976

[54] FINGERPRINT INKING DEVICE

[76] Inventors: Daniel L. Curtis, 1956 Ardmore Ave., Manhattan Beach, Calif. 90266; Allan D. Le Vantine, 18225 Rancho St., Tarzana, Calif. 91356

[22] Filed: Nov. 26, 1975

[21] Appl. No.: 635,602

[52] U.S. Cl. ................................ 118/6; 118/31.5; 118/264
[51] Int. Cl.² ........................................ A61B 5/10
[58] Field of Search ................... 118/31.5, 232, 233, 118/6, 205, 264; 427/1; 283/7; 156/1 NQ

[56] References Cited
UNITED STATES PATENTS

| | | | |
|---|---|---|---|
| 2,096,925 | 10/1937 | Seres, Jr. | 118/31.5 UX |
| 2,384,018 | 9/1945 | Doepner | 118/31.5 UX |
| 2,629,194 | 2/1953 | Johnson et al. | 118/31.5 |
| 2,746,192 | 5/1956 | Norton | 118/31.5 UX |
| 2,782,543 | 2/1957 | Soto | 118/31.5 |
| 3,405,006 | 10/1968 | Follrath | 118/115 X |
| 3,479,987 | 11/1969 | French | 118/31.5 |
| 3,694,240 | 9/1972 | Miller et al. | 118/31.5 |

FOREIGN PATENTS OR APPLICATIONS

| | | | |
|---|---|---|---|
| 686,243 | 1/1953 | United Kingdom | 118/205 |

*Primary Examiner*—Morris Kaplan

[57] ABSTRACT

A fingerprint inking apparatus, incorporating a self-contained supply of ink and a drive means that automatically produces a uniform film of ink of the correct thickness, on a thin elastic membrane, in preparation to the taking of rolled fingerprints. The membrane is supported on a compressible foam structure or between two rollers such that a downward pressure of the finger causes the membrane to form around the finger, thereby transferring the ink to the finger.

4 Claims, 2 Drawing Figures

U.S. Patent    July 27, 1976    3,971,335
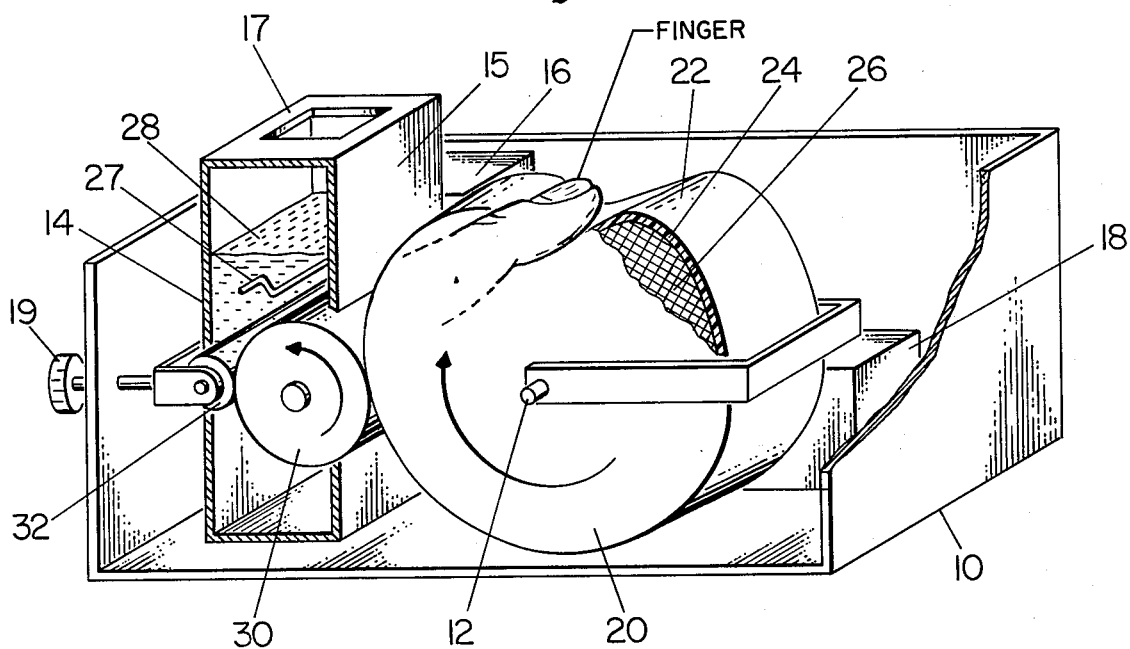
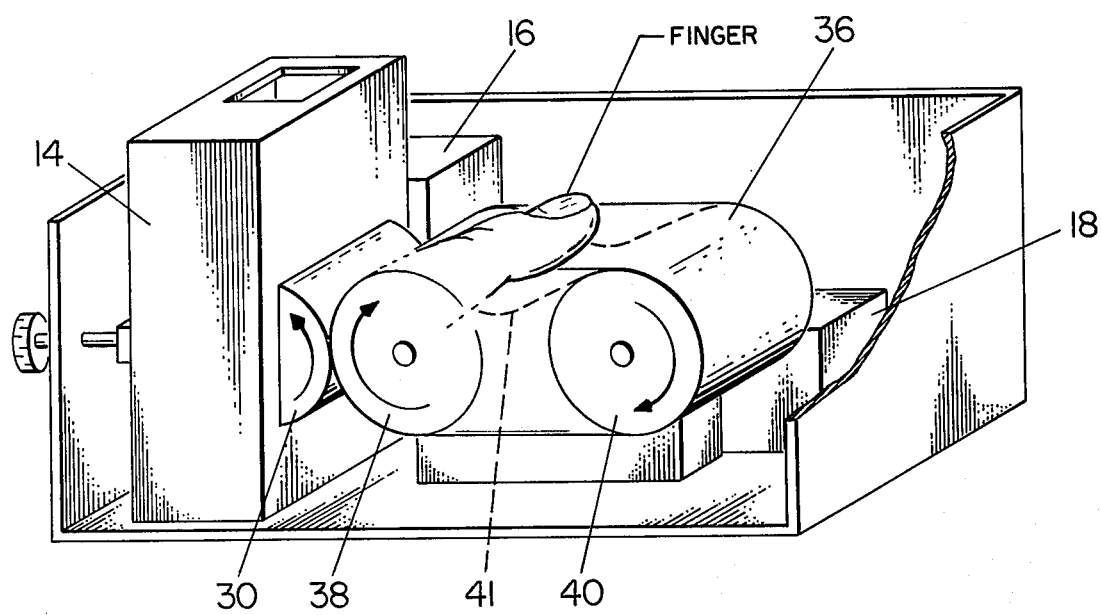

FINGERPRINT INKING DEVICE

This invention relates to the inking of fingers for the purpose of taking fingerprint impressions, and, more specifically, to a device for applying ink to the finger in preparation for the taking of rolled fingerprints.

The conventional method of inking the fingers in preparation to the taking of a set of rolled fingerprints is to manually roll each finger against a flat surface (usually glass) that has previously been prepared with a film of fingerprint ink. This action causes some of the ink film to be transferred to the finger. The inked finger is then rolled against a designated area of a card allowing some ink on the finger to transfer to the card and thereby leaving a characteristic rolled fingerprint on the card.

A second method is also used, U.S. Pat. No. 3,824,951, where the finger is held stationary and an inked surface is contact rolled in an epicyclical manner around the finger causing a film of ink to be deposited on the finger in preparation to the taking of a rolled fingerprint, the same relative motion occurring between the finger and the inking surface.

The quality of the resultant fingerprint is, to a large extent, dependent upon applying a uniform coating of ink of correct thickness on the finger in preparation for rolling the finger on the fingerprint card. In this conventional manual method of inking, a quantity of fingerprint ink is first applied to the flat inking surface and then a roller is used to spread the ink into a thin film covering a portion of the flat surface. This invariably leads to varying thicknesses of ink on the plate, depending upon the quantity of ink initially applied to the surface and to the extent that the ink is spread by the roller. The result is that varying amounts of ink are applied to the fingers leading to a varying of clarity and contrast in the resultant fingerprints. In addition, if the finger is allowed to slip as it is rolled on the inking surface, a localized build-up of ink will occur, filling the grooves in the finger and causing a poor quality print. It has been found in practice that skilled technicians, who are experienced in taking fingerprints, are reasonably proficient at producing high quality prints using this manual inking method. However, novice technicians have difficulty in repeatedly obtaining high quality fingerprints.

It is, accordingly, an objective of the present invention to provide an improved fingerprint inking apparatus.

It is yet another objective of the present invention to provide an improved fingerprint inking apparatus that uses a self-contained supply of ink and automatically places a uniform film of ink of the correct thickness on the finger in preparation to the taking of rolled fingerprints.

It is still another objective of the present invention to provide an improved fingerprint inking apparatus that allows the ink to be applied to the curved surfaces of the finger without requiring the finger to be rotated.

It is still another objective of the present invention to provide an improved fingerprint inking apparatus that will result in consistently higher quality fingerprints than is presently possible with the manual inking method.

Briefly stated, and in accordance with the presently preferred embodiment of the invention, a fingerprint inking apparatus is provided which includes a supply of ink in a suitable receptacle such that a thin film of ink is continuously present on the surface of a rotatable drum. The drum, in turn, is held in contact with a flexible elastic membrane such that when the membrane is moved past the drum, the rotatable drum transfers a thin film of ink to the membrane surface. As a second step in the operation of the apparatus, the inked surface membrane is stopped and the finger to be inked is pressed against the membrane such that the surface is caused to deform and wrap around the finger (approximately 180°). This action causes a portion of the ink on the membrane to be transferred to the contacted surface of the finger, in a thin uniform coating, such that a high quality fingerprint is obtained when the finger is rolled in a conventional manner on a fingerprint card.

For a complete understanding of the invention, together with an appreciation of other objectives and advantages thereof, please refer to the attached drawings and the following detailed description of the drawings, in which:

FIG. 1 is a perspective view of one embodiment of the invention with cut-away portions to show internal details;

FIG. 2 is a second embodiment of the invention, in perspective view, with cut-away sections.

The embodiment of the invention shown in FIG. 1 includes a compressible pillow-like cylindrical inking section 20 supported and rotatable on shaft 12 through its axis, an ink storage and dispensing mechanism 14, an electric drive motor 16, electrical control circuitry 18 and additional supporting and driving structures enclosed in housing 10.

In operation the finger to be inked is pressed downward against the surface 22 at the top of the inking section 20. Surface 22 has previously received a coating of ink having rolled in contact with the ink transfer roller 30 of the ink dispensing mechanism 14. A downward pressure of the finger, shown in FIG. 1, against the inked surface 20 causes the surface to be depressed forming around the finger and transferring the ink to the finger as required in preparation to the taking of a rolled fingerprint. In addition, the downward motion of the finger in compressing the inking section 20 causes the control circuitry 18 to be activated such that when the finger is removed from the inking section, the control circuitry activates the electrical drive motor 16 causing the inking section to rotate on shaft 12 so that a newly inked surface 22 of the inking section 20 is at the top position in preparation for the next fingerprint to be taken. During the same rotation another portion of surface 22 rolls in contact with ink transfer roller 30 and receives a fresh coating of ink.

The inking section 20 consists of a base structure 26 covered with a thin elastic membrane 24. The elastic membrane 24 is smooth and has the quality of a latex rubber sheet about the thickness and consistency of a surgeons glove rubber. The base structure 26 has the property of being spongy and relatively soft. "Supersoft" polyurethane foam has been found to be one material that has the desired properties for use as the base structure, in this embodiment of the invention. Other similar materials with suitable properties could be used equally as well for the elastic membrane or the base structure.

FIG. 1 also shows a very important aspect of the invention, as it illustrates that the entire portion of the finger to be printed is completely inked at one time. The combined properties of the elastic inking membrane 24 and the base structure 26 imparts sufficient pressure to all parts of the prescribed portion of the finger to simultaneously cause the required transfer of ink from the surface 22 to the finger. It is to be noted that this property of the inking surface of this invention is in contrast to the conventional method of inking the finger in preparation for taking rolled prints. In the conventional method the finger is rolled on a film of ink on a flat rigid plate. Ink is transferred to the finger by forcibly flattening the finger against the plate, portion by portion, as it is rolled across the plate. In this invention, however, the ink is transferred to the finger without distorting the finger and without rolling or rotating the finger.

Another important feature of this invention is the arrangement whereby ink is taken from the ink reservoir 28 of inker 14 and dispensed as a thin film of uniform thickness on transfer roller 30 for transfer to surface 22 of flexible elastic membrane 24 as cylindrical inking section 20 is rotated in contact with it.

Ink reservoir 28 is a box-like structure having four sides 15, and a top with an opening for replenishing ink 17 and a bottom comprised of a wiping roller (doctor roll) 32 and the transfer roller (roller applicator) 30. Transfer roller is driven by drive motor 16 at a suitable speed for the transfer of ink to inking section 20. Wiping roller 32 is driven opposite in rotation to roller 30 by means of a gear train, not shown, and at a rate such that the surface speed of roller 32 is slower than the surface speed of roller 30. In this embodiment of the invention, a surface speed of roller 32 at approximately ¼ the surface speed of roller 30 was found to be satisfactory. Thus there is a slipping motion between the surfaces of the rollers as they turn. This slipping motion, along with a suitable force F applied by screw 19 keeping the rollers in contact, causes a thin film of ink of uniform thickness to be spread across the surface of roller 30. The thickness of the film can be controlled by the force applied by screw 19. Agitator 27 within the ink reservoir is caused to oscillate back and forth by mechanical linkage, not shown, to maintain the ink in the reservoir in a semi-fluid state so that it will coat the rollers.

It has been found that transfer roller 30 can be made from any rigid material such as hard plastic or metal and should have a smooth surface. Wiping roller 32 is constructed of a rigid metal central cylinder covered with an outer layer of flexible rubber or plastic. The outer layer of flexible material on roller 32 conforms to the surface of roller 30 to provide the required slipping-rolling action. Although these are the preferred materials it is recognized that other materials may be used, and that one or the other, or both, of the rollers may be covered with a flexible material. It should be noted that this slipping-rolling action for dispensing a thin film of ink onto roller 30 is in contrast to previous arts for applying ink to rollers. Previous arts use many rollers rolling together in series to produce the uniform coating of ink. Some of these rollers also oscillate axially to promote uniformity. In this invention the sliding action between the rollers prevents the build-up of ink solids (i.e. carbon particles) which produce streaks and non-uniformities to the ink film on roller 30. Thus, a uniform ink film is produced in one operation by this invention, whereas previous arts require a multiplicity of operations to accomplish the same purpose.

A second embodiment of this invention is shown in FIG. 2. In this embodiment the finger inking apparatus consists of an ink coated elastic membrane of surgeons glove rubber or similar material, in the form of a belt 36 supported by two rollers 38 and 40. The finger to be inked is pushed downward against the top of the belt causing the membrane 36 to be depressed and stretched, as shown by broken line 41, as it forms around the finger. As all portions of belt 36 are under tension with finger in position 41, the surface of belt 36 is forced against the finger thereby transferring the ink from the belt to the prescribed surface area of the finger coinciding with that normally inked in preparation for the taking of a rolled fingerprint.

Prior to transferring ink from belt 36 to the finger, belt 36 is brought into contact with and rolled synchronously with in the direction shown in FIG. 2, ink transfer roller 30, of ink dispensing mechanism 14, applying a uniform coating of ink to belt 36. Both ink dispensing mechanism 14 and belt 36 are driven by drive motor 16 by means of mechanical coupling during this coating operation. At the completion of the belt coating operation rollers 38 and 40 are disengaged from any mechanical coupling and allowed to be free to rotate on their axes. This action permits the belt to stretch freely and uniformly around the finger during the finger inking procedure.

While the principles of the invention are thus disclosed, and the presently preferred embodiments of the invention are described in detail, it is not intended that the invention be limited to these embodiments. It is recognized that many modifications will occur to those skilled in the art which lie within the spirit and the scope of the invention. It is thus intended that the invention cover such modifications, and be limited in scope only by the appended claims.

What is claimed is:

1. In fingerprinting apparatus, a finger inking device comprising:
   an ink reservoir;
   a roller applicator operatively associated therewith and means for rotating said applicator in a first direction;
   a doctor roll operatively associated with said applicator and means for rotating said doctor in an opposed direction and at a lesser surface speed whereby to effect slippage between said rolls to produce a uniformly thin film of ink on said applicator;
   a movable, flexible, elastic, endless member operatively associated with said applicator, having the characteristic of conforming to a finger pressed thereupon, and adapted to be inked by said applicator upon relative movement therebetween;
   means to move said endless member to effect said inking of a continuous finite length thereupon; and
   each said means to move and to rotate being operative by means actuated by release of pressure of a finger being removed from said endless member; whereby a subsequent portion of said endless member is inked preparatory to a finger inking operation.

2. The apparatus of claim 1 wherein said endless member is an endless belt.

3. The apparatus of claim 1 wherein said endless member is a roller.

4. The apparatus of claim 1 wherein the thickness of the ink film on said roller applicator is regulated by the force holding the doctor roll in contact with the applicator as applied by a screw adjustment means.

* * * * *